US012134709B2

(12) United States Patent
Zweig

(10) Patent No.: US 12,134,709 B2
(45) Date of Patent: Nov. 5, 2024

(54) COATINGS FOR STERILIZATION WITH UV LIGHT

(71) Applicant: The Boeing Company, Chicago, IL (US)

(72) Inventor: Andrew Michael Zweig, Chesterfield, MO (US)

(73) Assignee: The Boeing Company, Chicago, IL (US)

(*) Notice: Subject to any disclaimer, the term of this patent is extended or adjusted under 35 U.S.C. 154(b) by 501 days.

(21) Appl. No.: 16/506,560

(22) Filed: Jul. 9, 2019

(65) Prior Publication Data
US 2021/0009819 A1 Jan. 14, 2021

(51) Int. Cl.
C09D 5/32 (2006.01)
A61L 2/10 (2006.01)
A61L 101/46 (2006.01)
C08K 5/00 (2006.01)
C08K 5/13 (2006.01)
C08L 27/18 (2006.01)
C08L 77/00 (2006.01)
C09D 5/14 (2006.01)
(Continued)

(52) U.S. Cl.
CPC ............ C09D 5/32 (2013.01); A61L 2/10 (2013.01); C09D 7/67 (2018.01); C09D 7/68 (2018.01); C09D 175/04 (2013.01); A61L 2101/46 (2020.08); A61L 2202/25 (2013.01); C08K 5/005 (2013.01); C08K 5/13 (2013.01); C08K 2201/003 (2013.01); C08K 2201/005 (2013.01); C08K 2201/011 (2013.01); C08L 27/18 (2013.01); C08L 77/00 (2013.01); C08L 2201/10 (2013.01); C09D 5/14 (2013.01)

(58) Field of Classification Search
None
See application file for complete search history.

(56) References Cited

U.S. PATENT DOCUMENTS 3,929,726 A * 12/1975 Schollenberger ........ C08K 5/13
528/48
3,978,156 A * 8/1976 Parker ..................... C08L 75/04
524/192
(Continued)

FOREIGN PATENT DOCUMENTS

CN 102676033 A * 9/2012
CN 106956486 7/2017
(Continued)

OTHER PUBLICATIONS

"Radiation: Ultraviolet (UV) Radiation" (https://www.who.int/news-room/questions-and-answers/item/radiation-ultraviolet-(uv) ) (2016 ) (Year: 2016).*
(Continued)

Primary Examiner — Vivian Chen
(74) Attorney, Agent, or Firm — Haynes and Boone, LLP

(57) ABSTRACT

Coating compositions that may be used in combination with UV light for sterilization include a polyurethane component and nanoparticles having an average particle size of from about 30 nm to about 400 nm. The nanoparticles absorb light having a wavelength of from about 100 nm to about 290 nm, and are present in an amount of less than about 25 weight percent of total solids in the coating composition.

9 Claims, 2 Drawing Sheets

(51) Int. Cl.
*C09D 7/40* (2018.01)
*C09D 175/04* (2006.01)

(56) References Cited

U.S. PATENT DOCUMENTS

| | | | | | |
|---|---|---|---|---|---|
| 4,307,000 | A | * | 12/1981 | Vasta | C08G 18/36 528/56 |
| 5,500,962 | A | * | 3/1996 | Tagg | E04H 1/1216 4/476 |
| 5,560,050 | A | * | 10/1996 | Tagg | A47K 11/02 4/449 |
| 5,682,622 | A | * | 11/1997 | Tagg | E04H 1/1216 4/449 |
| 6,200,680 | B1 | * | 3/2001 | Takeda | C03C 17/007 502/343 |
| 6,797,770 | B1 | * | 9/2004 | Mori | C08G 18/12 427/385.5 |
| 9,657,177 | B1 | | 5/2017 | Pringle et al. | |
| 9,828,497 | B2 | | 11/2017 | Higashira | |
| 9,976,038 | B2 | | 5/2018 | Pringle et al. | |
| 10,000,716 | B2 | | 6/2018 | Yu et al. | |
| 10,099,455 | B1 | * | 10/2018 | Hohenadel | B32B 27/10 |
| 2001/0031706 | A1 | | 10/2001 | Uchida | H05K 3/0058 508/100 |
| 2002/0071948 | A1 | * | 6/2002 | Duff | B82Y 30/00 428/323 |
| 2003/0004235 | A1 | * | 1/2003 | Wood | C07D 249/20 548/255 |
| 2005/0215663 | A1 | * | 9/2005 | Berge | B41J 2/01 523/160 |
| 2007/0275101 | A1 | * | 11/2007 | Lu | C09D 5/1625 514/642 |
| 2007/0297998 | A1 | * | 12/2007 | Meyer | A61K 8/27 424/59 |
| 2008/0124368 | A1 | * | 5/2008 | Sarangapani | A01N 25/10 424/405 |
| 2009/0297462 | A1 | | 12/2009 | Hessefort et al. | |
| 2010/0025642 | A1 | * | 2/2010 | Hanaki | C08K 5/005 252/588 |
| 2010/0115706 | A1 | * | 5/2010 | Bender | D06M 13/513 252/8.61 |
| 2011/0151244 | A1 | * | 6/2011 | Wu | C09D 7/61 106/287.19 |
| 2013/0231441 | A1 | * | 9/2013 | Robertson | B32B 27/00 524/590 |
| 2014/0213704 | A1 | * | 7/2014 | Amasaki | C08K 5/34926 544/212 |
| 2015/0044420 | A1 | * | 2/2015 | Nowak | C09D 7/61 428/141 |
| 2015/0177432 | A1 | * | 6/2015 | Hebrink | G02B 5/26 359/359 |
| 2015/0210864 | A1 | * | 7/2015 | Mahmoud | C08G 18/0823 524/548 |
| 2015/0252181 | A1 | * | 9/2015 | Higashira | C09D 5/022 524/507 |
| 2015/0259544 | A1 | * | 9/2015 | Lee | C09D 5/20 523/122 |
| 2015/0322656 | A1 | * | 11/2015 | Huang | E03D 9/14 4/209 R |
| 2016/0075887 | A1 | * | 3/2016 | Miki | C09D 133/08 522/36 |
| 2016/0096624 | A1 | * | 4/2016 | McIntosh | A47K 17/02 4/621 |
| 2017/0009084 | A1 | * | 1/2017 | Margel | C09D 5/1662 |
| 2017/0022440 | A1 | * | 1/2017 | Yu | C10M 125/26 |
| 2017/0073605 | A1 | * | 3/2017 | Sasaki | F16D 69/025 |
| 2017/0164734 | A1 | * | 6/2017 | Steele | A47B 88/487 |
| 2017/0175600 | A1 | * | 6/2017 | Douglass | C10M 145/22 |
| 2017/0247548 | A1 | * | 8/2017 | Pringle | C09D 5/004 |
| 2017/0283062 | A1 | * | 10/2017 | Childress | B08B 5/04 |
| 2017/0283092 | A1 | * | 10/2017 | Brown | B64F 5/30 |
| 2017/0333300 | A1 | * | 11/2017 | Enomura | A61K 8/0245 |
| 2019/0127963 | A1 | * | 5/2019 | Kim | B64D 11/02 |
| 2019/0144691 | A1 | * | 5/2019 | Enomura | C09C 1/3653 424/59 |
| 2019/0225821 | A1 | * | 7/2019 | Yoshii | C09D 201/00 |
| 2019/0281980 | A1 | * | 9/2019 | Prijic | B32B 37/18 |
| 2019/0367747 | A1 | * | 12/2019 | Enomura | C01G 49/02 |
| 2019/0382597 | A1 | * | 12/2019 | Gross | C09D 5/24 |

FOREIGN PATENT DOCUMENTS

| | | | |
|---|---|---|---|
| CN | 108359364 | | 8/2018 |
| CN | 108463746 | A | 8/2018 |
| CN | 108290780 | A | 1/2022 |
| EP | 3505580 | | 7/2019 |
| JP | 2000-198921 | A * | 7/2000 |
| JP | 2001215775 | A | 8/2001 |
| JP | 5653884 | B2 | 1/2015 |
| JP | 2017507192 | A | 3/2017 |
| KR | 101927995 | | 12/2018 |
| WO | WO 2010037076 | | 4/2010 |
| WO | WO 2014184989 | A1 | 11/2014 |
| WO | WO 2015012910 | | 1/2015 |

OTHER PUBLICATIONS

"Fluon PTFE" (Sep. 2011). (Year: 2011).*
"Lumacept", UVC coating system, Product Info, [retrieve on Jun. 26, 2019], Retrieved from the Internet: <URL: http://lumacept.com/?page_id=15>, 2 pages.
"UV in Healthcare, Advanced Ultraviolet Disinfection Proven to Reduce Hospital Acquired Infections", [retrieve on Jun. 26, 2019], Retrieved from the Internet: <URL: https://www.uvdi.com/>, 5 pages.
Castronuovo et al., "Effects of UV-C radiation on common dandelion and purple coneflower: First results", International Journal of Plant Biology 2017, vol. 8:7255, pp. 61-64, School of Agricultural, Forestry, Food and Environmental Sciences, University of Basilicata, Potenza, Italy.
Office Action for Chinese Patent Application No. 202010643267.8 dated Jul. 26, 2023; 10 pages.

* cited by examiner

COATINGS FOR STERILIZATION WITH UV LIGHT

BACKGROUND

1. Technical Field

The present disclosure relates to coatings and methods for disinfection of aircraft lavatories and other surfaces, and more particularly, to coatings that may be used in combination with ultraviolet (UV) light for disinfection.

2. Related Art

Current galley and lavatory cleaning is generally conducted by an airline cleaning company on a frequent basis, and typically during aircraft turn-around times. During these cleaning procedures, chemical disinfection is used to clean exposed surfaces, such as countertops, sinks, trolley doors, and floors. The interior of compartments may also be cleaned on a regular basis, such as ovens, chillers, storage containers, and so forth.

However, this process is time consuming, and there is a resulting need for improved techniques of cleaning and disinfecting aircraft.

SUMMARY

In accordance with examples of the present disclosure, various coating compositions and methods are provided for sterilization. Advantageously, the coating compositions allow sterilization of various surfaces using UV-C light while remaining transparent. The coating compositions protect the surfaces from UV-C light, but allow the UV-C light to kill or inactivate microorganisms on the surfaces.

In one aspect of the present disclosure, the coating composition includes a polyurethane component, and nanoparticles having an average particle size of from about 30 nm to about 400 nm. The nanoparticles absorb light having a wavelength of from about 100 nm to about 290 nm (i.e., UV-C light) and are present in an amount of less than about 25 weight percent of total solids in the coating composition. In several examples, the polyurethane component includes a crosslinked aliphatic polyurethane.

In certain examples, the nanoparticles include chemically inert and nonflammable particles. Suitable nanoparticles include, but are not limited to, metal oxides (e.g., titanium dioxide, tin oxide, silicon dioxide, or zinc oxide), polytetrafluoroethylenes (PTFE), or polyamides.

In various examples, the coating composition further includes a UV light blocking agent. Any suitable UV blocking agent may be used. In exemplary examples, a phenolic antioxidant is included in the coating composition.

Methods of applying a coating composition to an article include providing the coating composition described above and applying the coating composition to an external surface of the article.

In a second aspect of the present disclosure, an article includes a substrate having an external surface, and a coating composition on the external surface. The coating composition includes a crosslinked aliphatic polyurethane, and nanoparticles having an average particle size of from about 30 nm to about 400 nm. The nanoparticles absorb light having a wavelength of from about 100 nm to about 290 nm, and are present in an amount of less than about 25 weight percent of total solids in the coating composition.

In various examples, the substrate includes a metal or a plastic. In several examples, the nanoparticles include one or more of titanium oxide, zinc oxide, tin oxide, silicon oxide, a polytetrafluoroethylene (PTFE), or a polyamide.

In some examples, a method of sterilizing a surface includes exposing the external surface of the article to light having a wavelength of about 200 nm to about 240 nm. In certain examples, the coating composition is transparent on the external surface after exposure to light having a wavelength of about 200 nm to about 240 nm.

In a further aspect, a method includes providing a coating composition and applying the coating composition to a surface to be sterilized. The coating composition includes a crosslinked aliphatic polyurethane, and nanoparticles having an average particle size of from about 30 nm to about 400 nm. The nanoparticles absorb light having a wavelength of from about 100 nm to about 290 nm, and are present in an amount of less than about 25 weight percent of total solids in the transparent coating composition.

In some examples, the nanoparticles include one or more of titanium oxide, zinc oxide, tin oxide, silicon oxide, a polytetrafluoroethylene (PTFE), or a polyamide. In other examples, the coating composition further includes a UV light blocking agent.

In several examples, the method also includes exposing the surface to light having a wavelength of about 200 nm to about 240 nm. In some examples, the surface is exposed to light having a wavelength of about 220 nm in intermittent bursts.

In various examples, applying the coating composition includes spray applying. In certain examples, the surface to be sterilized includes one or more of a surface on and around a toilet inside a lavatory, a surface inside and around a sink inside a lavatory, a floor of a lavatory, a surface of a door handle, or a surface of a drawer handle or cabinet knob. The scope of the disclosure is defined by the claims, which are incorporated into this section by reference. A better understanding of the methods and formulations for coating compositions of the present disclosure, as well as an appreciation of the above and additional advantages thereof, will be afforded to those of skill in the art by a consideration of the following detailed description of one or more examples thereof. In this description, reference is made to the various views of the appended sheets of drawings, which are briefly described below, and within which, like reference numerals are used to identify like ones of the elements illustrated therein.

DETAILED DESCRIPTION

Figure 1:
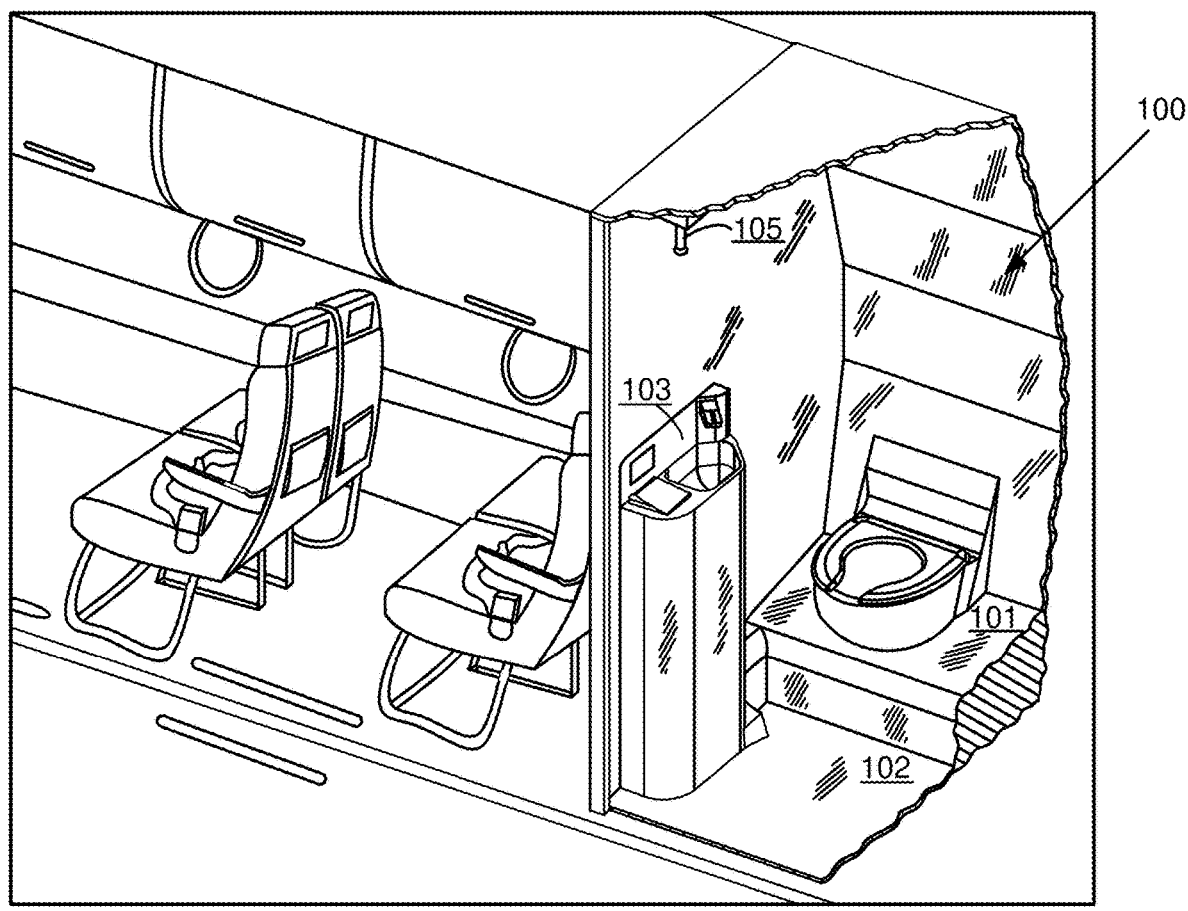
FIG. 1 illustrates a lavatory on an aircraft in accordance with an example of the present disclosure.

In aircraft lavatories, the toilets, countertops, cabinet doors, sinks and floors are cleaned by the cleaning company during aircraft turn-around and/or at the end of scheduled flight service. Aircraft lavatories provide an environment that is often considered unclean by passengers due to the possible presence of microbiological contamination. There may also be a perceived increased risk for transmissible disease from use of a lavatory, which are used by hundreds of users. Since various pathogens can live for weeks on hard surfaces, various viruses or bacterial infection may spread. Additionally, air traveler immune systems are constantly under assault from disruptions to circadian rhythms, stress, foreign environments, and so forth, which can escalate their vulnerability to various pathogens. As the pathogenic landscape continues to morph daily, it is desirable that decontamination of lavatories be addressed.

UV-C light is germicidal. It deactivates the DNA of bacteria, viruses, and other pathogens. UV-C light causes damage to the nucleic acid of microorganisms by forming covalent bonds between certain adjacent bases in the DNA. Their formation prevents the DNA from replication. When the microorganism tries to replicate, it dies.

UV-C light, however, has undesirable effects on plastics, paints, and coatings. Conventional coatings degrade or darken after repeated exposure to UV-C light, and more robust coatings, such as those used in hospitals, are opaque. Countertops and surfaces in the lavatory, are patterned to resemble granite or marble, and aircraft passengers do not want these patterns to be hidden with an opaque coating.

Accordingly, transparent coatings that can be sterilized with UV-C light without degradation or discoloration are described in the present disclosure.

The present disclosure describes coating compositions and methods that can be used to sterilize or disinfect surfaces, for example aircraft lavatory surfaces. The coating compositions include a base material and nanoparticles that do not interact with visible light so that the coating compositions do not appear hazy or colored when applied to different substrates such as metal or plastic. Different substrates that include the coating composition may be exposed to UV-C light and disinfected without degradation or discoloration. As used herein, UV-C light refers to ultraviolet C light having wavelengths of about 100 nm to about 290 nm.

In several examples, the base material of the coating compositions includes a polyurethane component, such as a crosslinked aliphatic polyurethane. Examples of exterior grade polyurethane coatings include PPG's Desothane® HS CA8000 Polyurethane Topcoat, AkzoNobel's Eclipse Semi-Gloss High Solids Decorative Topcoat, or Sherwin-Williams' Skyscapes® Clearcoat Topcoats.

The nanoparticles have an average particle size of from about 30 nm to about 400 nm. Thus, the nanoparticles have a particle size that is generally smaller than the wavelength of visible light (380-740 nm). Because of their size, the nanoparticles do not interact with visible light, and the coating compositions do not appear hazy or colored, but appear clear or transparent.

In addition, the nanoparticles absorb UV-C light and can convert the UV-C light to harmless infrared radiation (e.g., heat). In this way, the UV-C light does not interact with (e.g., degrade or destroy) the coating composition or the underlying substrate that the coating composition is applied on.

The concentration of nanoparticles needed to protect the surfaces of the substrate typically depends on the solids content of the coating. In illustrative examples, the nanoparticles are present in an amount of less than about 25 weight percent of total solids in the coating composition. For example, the nanoparticles may be present in an amount of about 5, 10, or 20 weight percent of the total solids in the coating composition, which can be sufficient for protecting the surface of the substrate, without interfering with the manufacturing, application of the coating, or the coating's resulting appearance, performance, or lifetime.

Suitable nanoparticles include inorganic particles that are chemically inert and nonflammable. Examples include metal oxide (e.g., titanium dioxide, tin oxide, silicon dioxide, or zinc oxide), a polytetrafluoroethylene (PTFE), or a polyamide (e.g., nylon). Inorganic particles are less soluble in cleaning agents (and are therefore less prone to leaching), can provide some abrasion or scuff resistance to the coating composition, do not result in colored breakdown products compared to organic particles, dissipate energy without degradation into smaller species or particles (no fragmentation), and are commercially available.

The coating compositions may be prepared using conventional methods. For example, a solution of the base material is prepared and then the appropriate amount of the inorganic particles is mixed in the solution to form the coating composition. Generally, the base material includes two parts that are mixed immediately prior to use. The smaller size of the inorganic particles may affect the viscosity of the coating composition, and therefore affect how well the coating composition can be applied or how fast the coating composition dries by evaporation of the solvent. This may require changing some of the solvent used to a slower blend (i.e., a solvent that evaporates more slowly), which can affect the rest of the solvent in the coating composition, and if spray applying, how the spray droplets form, coalesce, and dry. All of these factors can also affect the pot life (i.e., the amount of time it takes for an initial mixed viscosity to double). A person having ordinary skill in the art, with guidance from the present disclosure, is able to prepare an appropriate coating composition based on the desired viscosity of the coating composition.

The coating compositions may further include a UV blocking agent. A suitable UV blocking agent includes the IRGANOX® product. IRGANOX® is a trade name for BASF's phenolic antioxidants. These are characterized as having a phenolic group in which the two adjacent positions on the ring are substituted with tert-butyl groups. One example of the IRGANOX® product is the IRGANOX® 1010 product, shown below.

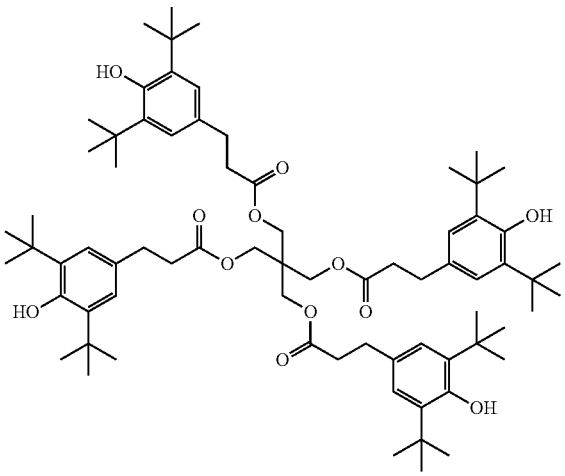

Referring now to the figures and, in particular, with reference to FIG. 1, an illustration of a lavatory 100 is depicted in accordance with an illustrative example. As depicted, lavatory 100 may be located in a vehicle. The vehicle may take the form of an aerospace vehicle, such as an aircraft, a spacecraft, a space shuttle, a space station, or some other type of aerospace vehicle. In other illustrative examples, the vehicle may take the form of a ground vehicle or a water vehicle, such as a bus, train, submarine, boat, or a ship.

As shown, the lavatory 100 includes a plurality of surfaces. Such surfaces may include any surfaces inside the lavatory 100 that may need to be disinfected due to the potential for contact with at least one of a person, animal, or object carrying any number of pathogens. Such pathogens can include air-borne pathogens from coughing, spitting, or any type of body fluid that could be released by a person or animal. The plurality of surfaces may include, for example, surfaces 101 on and around a toilet inside lavatory 100, surfaces 103 inside and around a sink inside lavatory 100, a floor of lavatory 101, one or more door handles, one or more drawer handles or cabinet knobs, and any other types of surfaces that can become infected through direct or indirect contact with at least one of a person, animal, or object.

To disinfect the surfaces in lavatory 100, different sources of UV-C light may be used. As shown, a UV-C light source 105 is disposed above the sink area 103, though it may be mounted to any surface inside the lavatory 100. In particular, the UV-C light source 105 may be mounted to a location that allows UV-C light emitted by the UV-C light source 105 to encounter the greatest number of surfaces inside the lavatory 100. Advantageously, the surfaces 101, 102, and 103 include the coating composition, which protects the surfaces 101, 102, and 103 from damage from UV-C light emitted by the UV-C light source 105. In an illustrative example, the UV-C light source 105 is selected as emitting a wavelength of about 200 nm to about 240 nm. In illustrative examples, the UV-C light source emits light having a wavelength of about 220 nm.

In most cases, the UV-C light source 105 is configured as an automatic light that is activated when the door to the lavatory 100 is closed and inactivated when the door is open to prevent passenger exposure when entering or leaving the lavatory 100. In some examples, a passenger may be offered an option to activate the disinfection process prior to entering the lavatory 100. Once the option is activated, the lavatory door locks automatically, preventing the passenger from entering the lavatory until the disinfection process is complete. The disinfection process is typically of short duration, e.g., a matter of seconds, and may take place in intermittent bursts, e.g., UV-C light is activated for 1-2 seconds, deactivated for 5 seconds, and UV-C light is activated again for 3-4 seconds. In case of an intrusion, the disinfection process may be aborted to protect the passenger's eyes from the UV-C light.

Once the surfaces 101, 102, and 103 are exposed to UV-C light from UV-C light source 105, UV-C light begins disinfecting the surfaces 101, 102, and 103. Disinfecting the surfaces 101, 102, and 103 includes destroying potential pathogens that may be present on the surfaces 101, 102, and 103. The crucial hydrogen bonds that link the DNA chain of the pathogens together rupture when exposed to UV-C light.

Figure 2:
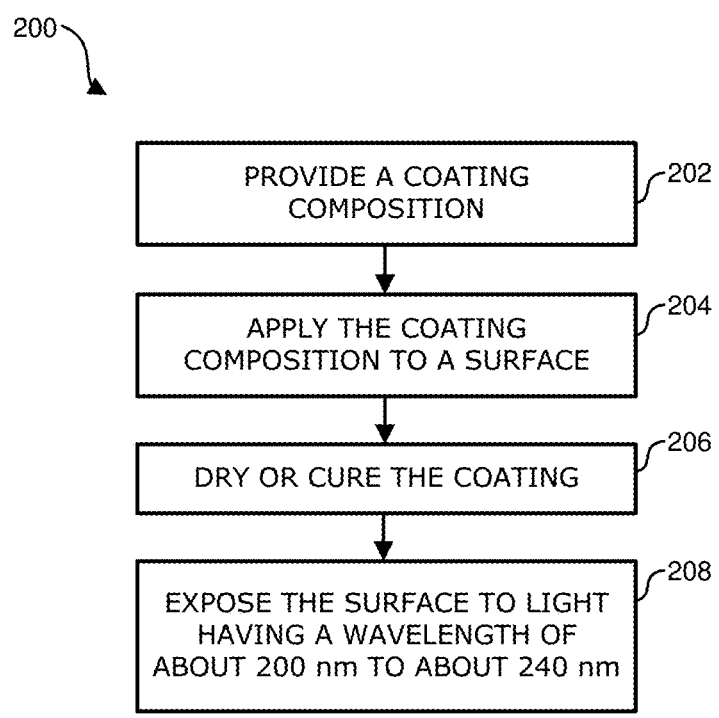
FIG. 2 illustrates an example process for sterilizing the surface of an article in accordance with an example of the present disclosure.

FIG. 2 shows an example process of applying the coating composition to an article. In block 202, the coating composition is provided. In block 204, the coating composition is applied to an external surface of the article. Any suitable article having an external surface to be disinfected may include the coating composition. Examples include toilets, sinks, floors, countertops, table tops, cabinet doors, door knobs, faucets, and walls.

The coating composition can be applied by manual application or by spray application. For example, the coating composition may be loaded into a spray gun or other type of spray applicator, and then sprayed onto the surface to be coated.

In block 206, the coating composition is dried or cured (or otherwise solidified). For example, the coating composition can be dried at room temperature or at an elevated temperature (e.g., 30-40° C.). In other examples, infrared (IR) heating by heat lamps, or use of UV light, which crosslinks various reactive species in the coating composition, may be used.

In block 208, once the coating composition is dried or cured, the surface may be sterilized with UV-C light having a wavelength of about 200 nm to about 240 nm. Advantageously, the coating composition remains transparent on the external surface of the article even after exposure to light having a wavelength of about 200 nm to about 240 nm. The nanoparticles in the coating composition absorb the UV-C light, rather than reflecting the UV-light.

When introducing elements of the present invention or exemplary aspects or example(s) thereof, the articles "a," "an," "the," and "said" are intended to mean that there are one or more of the elements. The terms "comprising," "including," and "having" are intended to be inclusive and mean that there can be additional elements other than the listed elements. Although this invention has been described with respect to specific examples, the details of these examples are not to be construed as limitations. Different aspects, examples and features are defined in detail herein. Each aspect, example or feature so defined can be combined with any other aspect(s), example(s) or feature(s) (preferred, advantageous or otherwise) unless clearly indicated to the contrary. Examples described above illustrate but do not limit the invention. It should also be understood that numerous modifications and variations are possible in accordance with the principles of the present disclosure. Accordingly, the scope of the invention is defined only by the following claims.

What is claimed is:

1. An article comprising:
   a substrate having an external surface; and
   a coating composition on the external surface, wherein the coating composition consists of:
      a crosslinked aliphatic polyurethane; and
      nanoparticles having an average particle size of from about 30 nm to about 400 nm and absorbing light having a wavelength of from about 100 nm to about 290 nm, wherein the nanoparticles are present in an amount of about 5, 10, or 20 weight percent of total solids in the coating composition and the nanoparticles consist of one or more of a polytetrafluoroethylene (PTFE) or a polyamide, and
   optionally an ultraviolet (UV) light blocking agent,
   wherein the article comprises a toilet, a sink, a floor, a countertop, a table top, a cabinet door, a door handle, a faucet, a drawer handle, or a cabinet knob, each article located inside an aircraft lavatory.

2. The article of claim 1, wherein the coating composition is transparent on the external surface after exposure to light having a wavelength of about 200 nm to about 240 nm.

3. The article of claim 1, wherein the substrate comprises a metal or a plastic.

4. A method of sterilizing a surface, comprising exposing the external surface of the article of claim 1 to light having a wavelength of about 200 nm to about 240 nm.

5. The article of claim 1, wherein the UV light blocking agent is present.

6. The article of claim 5, wherein the UV light blocking agent comprises a phenolic antioxidant.

7. The article of claim 6, wherein the phenolic antioxidant comprises a phenolic group in which two adjacent positions to the hydroxyl group on a ring of the phenolic group are substituted with tert-butyl groups.

8. The article of claim 1, wherein the nanoparticles are present in an amount of about 10 weight percent of total solids in the coating composition.

9. The article of claim 1, wherein the nanoparticles are present in an amount of about 20 weight percent of total solids in the coating composition.

* * * * *